(12) United States Patent
Okazaki (10) Patent No.: US 7,618,542 B2
(45) Date of Patent: Nov. 17, 2009

(54) BLOOD PURIFYING DEVICE AND METHOD OF OPERATING THE SAME

(75) Inventor: Soichirou Okazaki, Shizuoka (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 720 days.

(21) Appl. No.: 10/523,968

(22) PCT Filed: Aug. 4, 2003

(86) PCT No.: PCT/JP03/09878

§ 371 (c)(1),
(2), (4) Date: Dec. 2, 2005

(87) PCT Pub. No.: WO2004/014463

PCT Pub. Date: Feb. 19, 2004

(65) Prior Publication Data

US 2006/0124548 A1    Jun. 15, 2006

(30) Foreign Application Priority Data

Aug. 8, 2002    (JP)    ............................. 2002-231007

(51) Int. Cl.
*B01D 61/32*    (2006.01)
*B01D 61/26*    (2006.01)
*B01D 61/28*    (2006.01)
(52) U.S. Cl. ........................... 210/739; 210/85; 210/86; 210/97; 210/103; 210/104; 210/134; 210/143; 210/252; 210/257.1; 210/257.2; 210/258; 210/645; 210/646; 210/744; 604/4.01; 604/5.01; 604/6.09; 604/6.11; 604/9; 604/28; 604/65; 604/67

(58) Field of Classification Search .................. 210/645, 210/646, 739, 744, 85, 86, 97, 103, 104, 210/134, 143, 252, 257.1, 257.2, 258; 604/4.01, 604/5.01, 6.09, 6.1, 6.11, 9, 28, 65, 67
See application file for complete search history.

(56) References Cited

U.S. PATENT DOCUMENTS 5,698,090 A    12/1997    Bene et al.

FOREIGN PATENT DOCUMENTS

DE    3132790    3/1983

(Continued)

OTHER PUBLICATIONS

English Translation of Japanese Patent Publication No. 9-239024.*

*Primary Examiner*—John Kim
(74) *Attorney, Agent, or Firm*—Young & Thompson (57) ABSTRACT

A blood purifying apparatus particularly suitable for continuous blood purification, and a method of controlling the same whereby the weight of body fluid removed from a patient and a feed weight to the patient can be more accurately controlled. A blood purifying apparatus 50 adapted for the continuous blood purification includes a drain C, a dialysate feed A, and a replacement fluid feed B, which are equipped with transfer pumps 5, 6, 7, respectively, reservoir containers 8, 9, and 10, respectively, that are capable of storing a predetermined volume, and fluid level sensors 11, 12, and 13, respectively. The blood purifying apparatus further includes a single weight-meter 20 capable of measuring the reservoir containers 8, 9, and 10 all at the same time.

9 Claims, 3 Drawing Sheets

FOREIGN PATENT DOCUMENTS

| | | |
|---|---|---|
| DE | 19846776 | 11/1999 |
| EP | 0373455 | 6/1990 |
| EP | 0 722 744 | 7/1996 |
| JP | 63-25804 | 2/1988 |
| JP | 3-80028 | 12/1991 |
| JP | 4-70909 | 11/1992 |
| JP | 9-239024 | 9/1997 |
| WO | 98/50091 | 11/1998 |
| WO | 00/51664 | 9/2000 |

\* cited by examiner

PRIOR ART

BLOOD PURIFYING DEVICE AND METHOD OF OPERATING THE SAME

FIELD OF THE INVENTION

The present invention relates to a blood purifying apparatus and a method of controlling the apparatus, particularly to a blood purifying apparatus and a method of controlling the apparatus suitable for the generically called continuous blood purification, such as continuous hemofiltration, continuous hemodialysis, and continuous hemodiafiltration.

BACKGROUND ART

In renal failure patients, normally urine volumes decrease due to deterioration of renal function, often resulting in overhydration. A treatment is therefore required that would pass the blood of the patient through an extracorporeal circulation so that the condition of their body's water can be as nearly normalized as possible. This process of removing water from the body is referred to as "body fluid removal." Because the total body fluid variation amount is managed based on the removal weight of body fluid during treatment, the removal weight of body fluid is considered the most important parameter in patient management.

In recent years, for the treatment of renal failure or multiple organ failure with serious complications in the circulatory system, the generically called continuous blood purification has proved effective in the areas of emergency and intensive care. The continuous blood purification includes continuous hemofiltration (to be hereafter referred to simply as CHF), continuous hemodialysis (to be hereafter referred to simply as CHD), and continuous hemodiafiltration (to be hereafter referred to simply as CHDF).

CHF is a technique whereby blood is caused to flow in a blood purifying apparatus accommodating a semipermeable membrane in order to expel water containing waste products through the filtering membrane while delivering replacement fluid to the body continuously and slowly. CHD is a technique whereby dialysis for achieving an acid-base equilibrium by osmosis, for example, is performed continuously and slowly. CHDF is a technique combining CHF and CHD, whereby, in order to improve the small molecular-weight removal performance of CHF, a dialysate is caused to flow on the filtrate side of the blood purifying device so that a dialysis effect can be obtained. In any of these blood purifying methods, the continuous and slow treatment is characterized in that, as the name suggests, a single treatment is conducted over several days and blood purification is carried out slowly. Such a treatment greatly differs from the simple hemodialysis or hemofiltration in terms of temporal magnitude, the latter techniques requiring 4 to 5 hours for a single treatment.

A preferable example of a blood purifying apparatus based on the aforementioned continuous blood purification is disclosed in JP Patent Publication (Kokai) No. 9-239024 A. The apparatus comprises at least either a means for feeding a dialysate for hemodialysis or a means for feeding a replacement fluid for hemofiltration, a drain means, and a blood circulation path. Each of the means is equipped with a reservoir container, a fluid transfer pump, and a plurality of weightmeters for weighing the reservoir container. Based on the information provided by each of the weightmeters, the flow rate of each fluid transfer pump is individually controlled. Another example suitable for CHF or CHD is disclosed in JP Patent Publication (Kokai) No. 4-70909 A. The example comprises at least either a means for feeding a dialysate for hemodialysis or a means for feeding a replacement fluid for hemofiltration, a drain means, and a blood circulation path. Each of the means is equipped with a reservoir container and a fluid transfer pump, the reservoir container being provided with a fluid level sensor for detecting an upper limit and a lower limit of the stored quantity of the reservoir container. The apparatus further comprises a single weightmeter for weighing two reservoir containers all at the same time. Based on the information provided by the weightmeter, the flow rate of fluid transfer pump is individually controlled.

Figure 3:
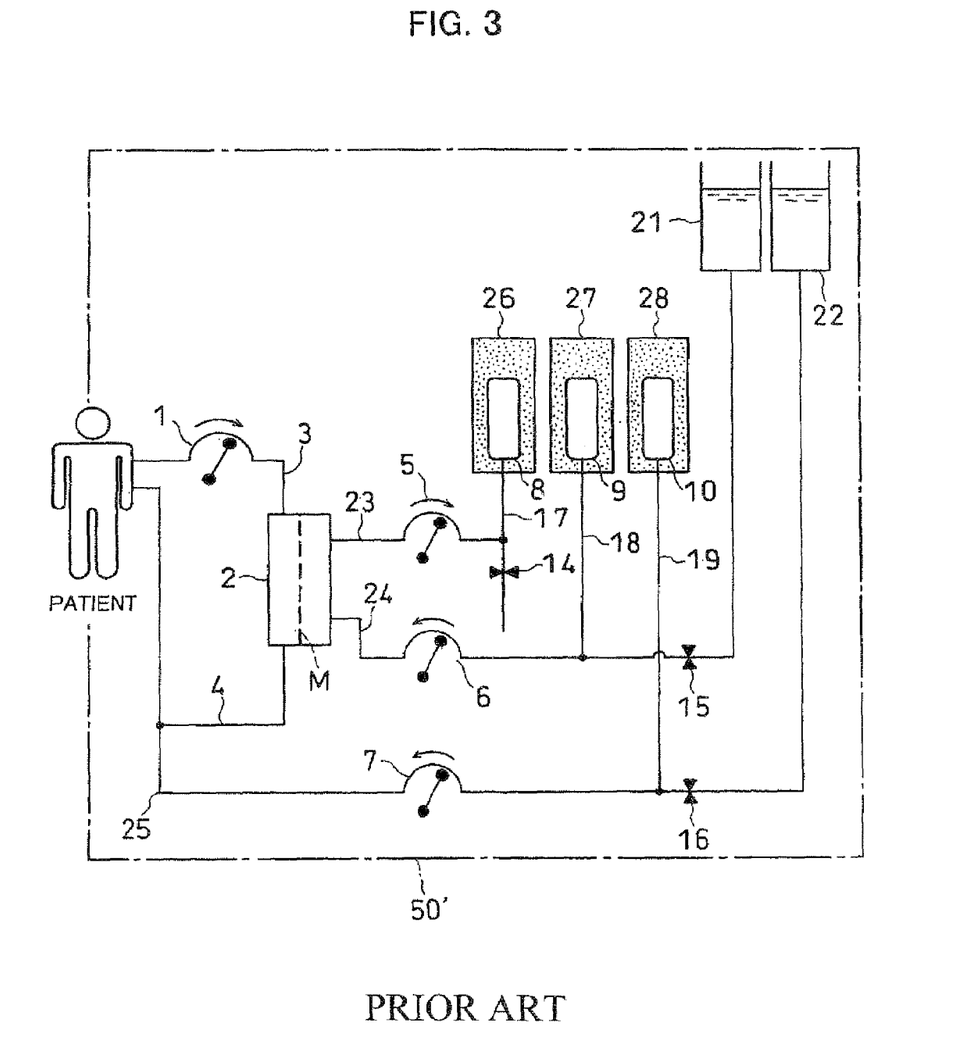
FIG. 3 schematically shows an example of a conventional blood purifying apparatus.

FIG. 3 shows the concept of the blood purifying apparatus of the aforementioned first example, which is based on the continuous blood purification. A blood purifying apparatus 50' is comprised of a blood drawing line 3 and a blood retransfusing line 4, which together form a blood circulation path; a drain line 23 for draining water containing waste products; a replacement fluid line 25 connected to the blood retransfusing line 4 for delivery of replacement fluid to the patient; and a dialysate feeding line 24 for feeding a dialysate to the filtrate side within the blood purifying device 2. In the blood drawing line 3, there is provided a blood pump 1. A blood purifying device 2, which includes a filtration membrane M, is disposed between the blood drawing line 3 and the blood retransfusing line 4.

The drain line 23 includes a drain transfer pump 5 for draining a filtrate and dialysis drain fluid from the blood purifying device 2, a drain reservoir container 8 connected to a drain branch line 17 that branches off on the outlet side of the drain transfer pump 5; and a shutoff valve 14 attached to the drain line 23 downstream of the branch portion. The drain reservoir container 8 is equipped with a weightmeter 26 for drainage weighing purposes.

The dialysate line 24 includes a transfer pump 6 for feeding a dialysate to the filtrate side within the blood purifying device 2; a dialysate reservoir container 9 connected to a dialysate branch line 18 that branches off on the inlet side of the dialysate transfer pump 6; and a shutoff valve 15 attached to the dialysate transfer line 24 upstream of the branch portion. The dialysate reservoir container 9 is equipped with a weightmeter 27 for dialysate weighing purposes.

The replacement fluid line 25 includes a transfer pump 7 for feeding a replacement fluid to the patient; a replacement fluid reservoir container 10 connected to a replacement branch line 19 branching off on the inlet side of the replacement fluid transfer pump 7; and a shutoff valve 16 attached to the replacement fluid line 25 upstream of the branch portion. The replacement fluid reservoir container 10 is equipped with a weightmeter 28 for weighing the replacement fluid.

The blood taken out from a patient using the blood pump 1 passes through the blood drawing line 3 and is then introduced into the blood purifying device 2 including the filtration membrane M, where waste products or the like are removed. In the blood purifying device 2, where a dialysate is supplied by the transfer pump 6 for dialysate, an acid-base equilibrium, for example, is established, and the filtrate and dialysis drain fluid are drained by the drain transfer pump 5. The blood that has been subjected to filtration and dialysis in the blood purifying device 2 is then returned to the patient via the blood retransfusing line 4, in the course of which a replacement fluid of substantially an equal weight to that of the filtrate is added by the replacement fluid transfer pump 7, thus delivering the replacement fluid to the patient.

The device thus does not require frequent weighing or adjustment operations by the staff, and is capable of continuously performing treatment in a safe manner while appropriately controlling the body fluid weight of the patient. Furthermore, a dialysate reservoir unit 21 or a replacement fluid reservoir unit 22 can be exchanged as needed, or, in the case where the filtrate and dialysis drain fluid are collected in a tank, the tank can be exchanged as needed, without directly affecting the measurement of the weight of removed body fluid or without terminating the treatment.

The transfer pumps are associated with certain amounts of flow rate errors. In order to minimize the influence of such errors, in the above-described apparatus, the reservoir containers 8, 9, and 10 are equipped with the weightmeters 26, 27, and 28, respectively, so that data can be supplied from the individual weightmeters to a control unit, which is not shown. The control unit monitors the data from the weightmeters 26, 27, and 28 at all times, and calculates the actual flow rate based on a change in weight per unit time. If it finds a difference between the actual flow rate and a set flow rate, the control unit automatically adjusts the rotation speed of a motor in each of the transfer pumps 5, 6, and 7 individually, such that the set flow rate equals the actual flow rate so as to maintain a flow rate accuracy.

Although the above-described apparatus is capable of maintaining a high flow rate accuracy, it inevitably suffers from errors on the order of 1% in the flow rate accuracy in each transfer pump in actual operations, due to factors such as the temperature characteristics of the weight sensors and of the measurement electronic circuitry, variations with time, methods of adjustment during manufacture, variations in the shape of each reservoir container, and so on.

As described above, the weight of body fluid removed from a renal failure patient $\Delta V(L)$, which is managed as an important parameter, is determined by the following equation:

$$\Delta V = V_F - V_C - V_D \quad (1)$$

where $V_F$ (L) is the amount of fluid drained by the drain transfer pump 5, $V_C$ (L) is the amount of replacement fluid supplied by the replacement fluid transfer pump 7, and $V_D$ (L) is the weight of dialysate supplied by the dialysate feed pump 6.

Conventionally, when performing a treatment based on CHDF, the flow rate of the transfer pumps is generally on the order of 1 L/hr. For example, if the flow rate of the drain transfer pump 5 is set at 1 L/hr, that of the replacement fluid transfer pump 7 at 0.5 L/hr, and that of the dialysate transfer pump 6 at 0.5 L/hr, then $V_F = 24 \pm 0.24$ (L), $V_C = 12 \pm 0.12$ (L), and $V_D = 12 \pm 0.12$ (L) in 24 hours, assuming that each transfer pump has a flow rate error of approximately 1%. In this case, if the removal weight of body fluid $\Delta V$ is calculated according to equation (1), $\Delta V = 0 \pm 0.48$ (L), thus indicating that the body fluid removal error can be reduced to approximately 0.48 (L) or less, which corresponds to 2% of the drained volume $V_F$.

DISCLOSURE OF THE INVENTION

In recent years, when performing a treatment based on CHDF or the like, in order to improve the efficiency of the treatment, the flow rate of transfer pumps are increasingly often set at a high level, such as on the order of 10 L/hr. In such a case, if the flow rate of the drain transfer pump 5 is set at 10 L/hr, that of the replacement fluid transfer pump 7 at 5 L/hr, and that of the dialysate transfer pump 6 at 5 L/hr in a conventional apparatus with a flow rate error on the order of 1% in each transfer pump, then $V_F = 240 \pm 2.4$ (L), $V_C = 120 \pm 1.2$ (L), and $V_D = 120 \pm 1.2$ (L) in 24 hours. In this case, if the removal weight of body fluid $\Delta V$ is calculated according to equation (1), $\Delta V = 0 \pm 4.8$ (L), thus indicating a body fluid removal error of as much as about 4.8 L, which corresponds to 2% of the drained volume $V_F$.

When there are such large errors, a problem could arise where the blood purifying procedure increases the risk of the body fluid balance of the patient becoming abnormal, rather than providing the intended therapeutic effect. Although in reality such a problem is prevented by performing a mutual feedback control and the patient is subject to no adverse effects, it is nevertheless desired to minimize the body fluid removal error without performing such a feedback control.

Thus, the inventors came to realize that there was a need for some means for calculating and controlling the flow rate of each transfer pump with high accuracy in order to manage the removal weight of body fluid more accurately than before in accordance with the continuous blood purification. In accordance with the aforementioned conventional technique, however, the flow rate accuracy is maintained for each transfer pump. Therefore, in order to more accurately manage the removal weight of body fluid, the flow rate accuracy of each pump must be improved to the order of 0.1%. The maximum flow rate accuracy achievable by the current technology, however, is on the order of 1%.

The blood purifying apparatus disclosed in JP Patent Publication (Kokai) No. 4-70909 A (1992) comprises one weightmeter for weighing two reservoir containers all at the same time, wherein each transfer pump is individually controlled on the basis of the information provided by the weightmeter. As a result, the flow rate error can be reduced to some extent as compared with the example in which two weightmeters are disposed for each reservoir container. However, in this blood purifying apparatus, it is necessary to combine conventional dialysis apparatuses when performing a hemodialysis, which leads to unsatisfactory flow rate accuracy in the removal weight of body fluid and to a complicated structure of the system. Hence, there is a need for further improvements.

In view of the aforementioned problems of the prior art, it is therefore an object of the invention to provide a blood purifying apparatus particularly suitable for the continuous blood purification, and a method of controlling the same, whereby, upon treatment of a renal disease or multiple organ failure patient, the removal weight of body fluid in the patient as well as the transfer volume to the patient can be more accurately managed.

Figure 1:
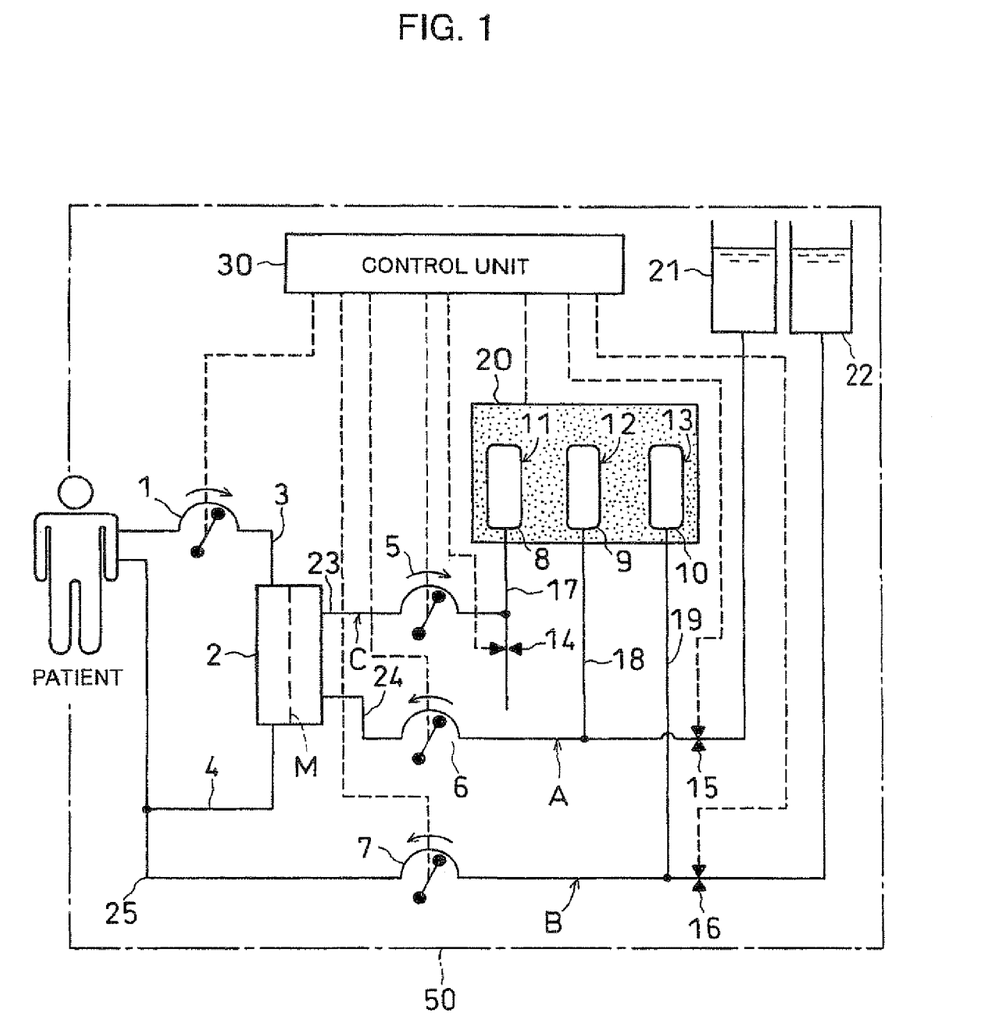
FIG. 1 schematically shows an embodiment of the blood purifying apparatus according to the invention.

In order to achieve the aforementioned object, the invention provides the following:

1. A blood purifying apparatus 50 comprising a dialysate feed means A, a replacement fluid feed means B, a drain means C, a blood purifying device 2, and a blood circulation path consisting of a blood drawing line 3 and a blood retransfusing line 4, wherein:

said dialysate feed means A comprises: a dialysate transfer line 24 of which one end is connected to said blood purifying device 2 and the other end connected to a dialysate reservoir unit 21; a dialysate transfer pump 6 disposed in the line; a dialysate reservoir container 9 connected to a dialysate branch line 18 branching off on an inlet side of said dialysate transfer pump 6; and a shutoff valve 15 attached to said dialysate transfer line upstream of a branch portion;

said replacement fluid feed means B comprises: a replacement fluid feed line 25 of which one end is connected to said blood retransfusing line 4 and the other end connected to a replacement fluid reservoir unit 22; a replacement fluid transfer pump 7 disposed in the line; a replacement fluid reservoir container 10 connected to a replacement fluid branch line 19 branching off on an inlet side of said replacement fluid transfer pump 7; and a shutoff valve 16 attached to said replacement fluid line 25 upstream of a branch portion;

said drain means C comprises: a drain line 23 of which one end is connected to said blood purifying device 2 and the other end opened; a drain transfer pump 5 disposed in the line;

a drain reservoir container 8 connected to a drain branch line 17 branching off from an outlet side of said drain transfer pump 5; and a shutoff valve 14 attached to said drain line 23 downstream of a branch portion, wherein the three reservoir containers 8, 9, and 10 are equipped with fluid level sensors 11, 12, and 13, said apparatus further comprising a weightmeter 20 for weighing the said three reservoir containers 8, 9, and 10 all at the same time, and a control unit 30 for controlling the opening and closing of said shutoff valves 14, 15, and 16, and the pump flow rate of each of said transfer pumps 6, 7, and 5.

2. The aforementioned blood purifying apparatus, wherein the individual fluid level sensors 11, 12, and 13 detect an upper limit of a fluid in each of said reservoir containers 8, 9, and 10.

Figure 2:
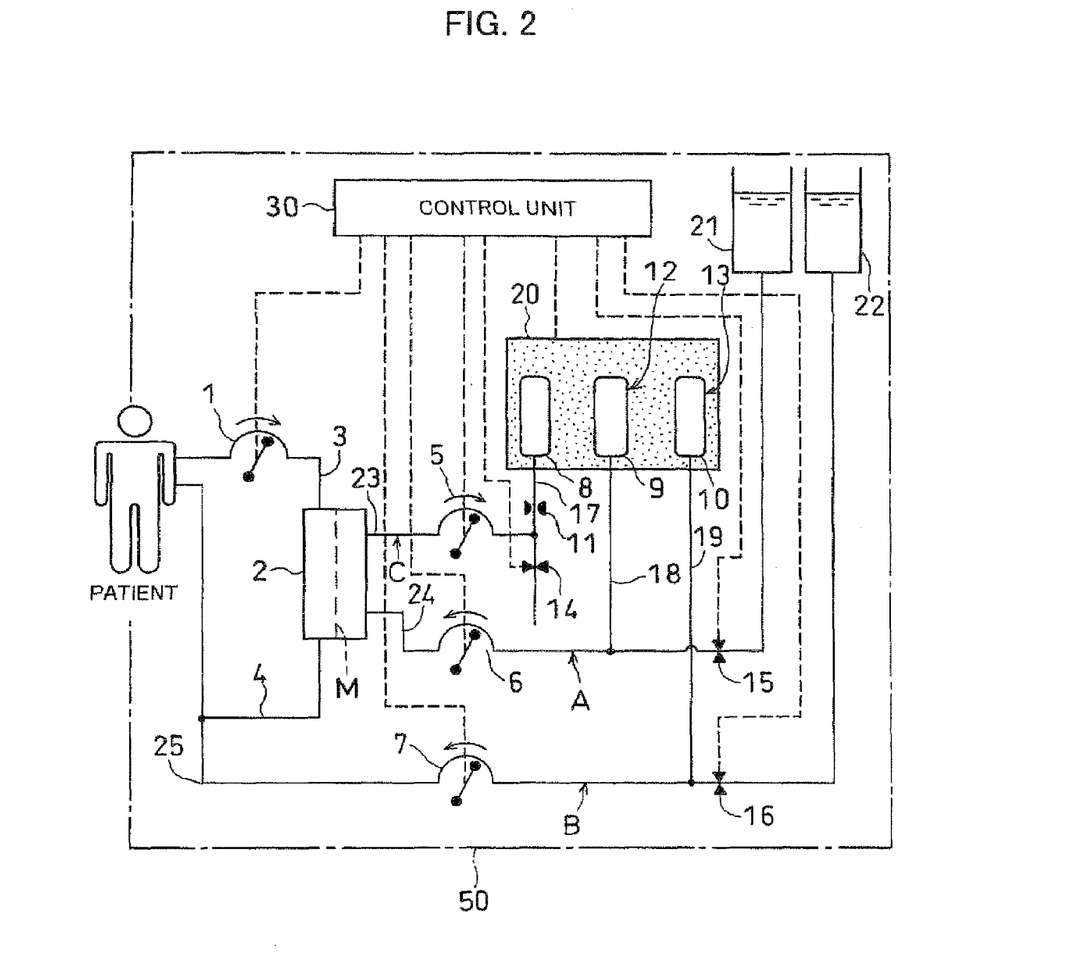
FIG. 2 schematically shows another embodiment of the blood purifying apparatus of the invention.

3. The aforementioned blood purifying apparatus, wherein the fluid level sensor 11 for said drain reservoir container 8 detects a lower limit of a fluid in said drain reservoir container 8, and the fluid level sensors 12 and 13 for said dialysate reservoir container and the replacement fluid reservoir container detect an upper limit of fluids in said dialysate reservoir container 9 and the replacement fluid reservoir container 10.

The aforementioned blood purifying apparatus, wherein said control unit 30 performs a removed body fluid weight measuring phase consisting of:

a first phase in which the shutoff valves 15, 16, and 17 are opened, whereby said dialysate reservoir container 9 and said replacement fluid reservoir container 10 are each filled with a fluid while at the same time a fluid is discharged from said drain reservoir container 8; and a second phase in which said apparatus is controlled with each of said shutoff valves 15, 16, and 17 closed, and a change in the total fluid weight in said dialysate reservoir container 9, said replacement fluid reservoir container 10, and said drain reservoir container 8 during the operation of said apparatus is acquired from information provided by said weightmeter 20 in order to weigh the removal weight of body fluid, wherein said control unit 30 controls the flow rate of at least one of the transfer pumps such that a desired removal weight of body fluid can be obtained in said second phase.

5. The aforementioned blood purifying apparatus, wherein said control unit 30 performs a feed weight measuring phase consisting of:

a third phase in which each of said shutoff valves 15, 16, and 17 is opened, whereby said dialysate reservoir container 9 and said replacement fluid reservoir container 10 are filled with individual fluids while at the same time a fluid is discharged from said drain reservoir container 8; and a fourth phase in which said apparatus is controlled with only the shutoff valve 15 for said dialysate feed means A and the shutoff valve 16 for said replacement fluid feed means B closed, and in which a change in the total fluid weight in said dialysate reservoir container 9, said replacement fluid reservoir container 10, and said drain reservoir container 8 is acquired from information provided by said weightmeter 20 so as to calculate a feed weight which is the sum of the weight of replacement fluid and the weight of the dialysate, wherein said control unit 30 controls the flow rate of the dialysate transfer pump and the replacement fluid transfer pump such that a desired feed weight can be obtained during the fourth phase.

6. The aforementioned blood purifying apparatus, wherein a flow rate control is performed based on an arbitrary combination of said removed body fluid weight measuring phase and said feed weight measuring phase.

7. The aforementioned blood purifying apparatus, wherein a flow rate control is performed by alternately repeating said removed body fluid weight measuring phase and said feed weight measuring phase.

8. The aforementioned blood purifying apparatus, wherein said apparatus is of a continuous and slow type.

In order to achieve the objective, the invention further provides:

9. A method of controlling the aforementioned blood purifying apparatus, said method comprising performing a removed body fluid weight measuring phase consisting of:

a first phase in which the shutoff valves 15, 16, and 17 are opened, whereby said dialysate reservoir container 9 and said replacement fluid reservoir container 10 are each filled with a fluid while at the same time a fluid is discharged from said drain reservoir container 8; and a second phase in which said apparatus is controlled with each of said shutoff valves 15, 16, and 17 closed, and a change in the total fluid weight in said dialysate reservoir container 9, said replacement fluid reservoir container 10, and said drain reservoir container 8 during the operation of said apparatus is acquired from information provided by said weightmeter 20 in order to weigh the removal weight of body fluid, wherein said control unit 30 controls the flow rate of the transfer pumps 6, 7, and 5 such that a desired removal weight of body fluid can be obtained in said second phase.

10. A method of controlling the aforementioned blood purifying apparatus, said method comprising performing a feed weight measuring phase consisting of:

a third phase in which each of said shutoff valves 15, 16, and 17 is opened whereby said dialysate reservoir container 9 and said replacement fluid reservoir container 10 are filled with individual fluids while at the same time a fluid is discharged from said drain reservoir container 8; and a fourth phase in which said apparatus is controlled with only the shutoff valve 15 for said dialysate feed means A and the shutoff valve 16 for said replacement fluid feed means B closed, and in which a change in the total fluid weight in said dialysate reservoir container 9, said replacement fluid reservoir container 10, and said drain reservoir container 8 is acquired from information provided by said weightmeter 20 so as to calculate a feed weight which is the sum of the weight of replacement fluid and the weight of the dialysate, wherein:

said control unit 30 controls the flow rate of the dialysate transfer pumps 6, 7, and 5 such that a desired feed weight can be obtained during the fourth phase.

11. A method of controlling the aforementioned blood purifying apparatus, said method comprising an arbitrary combination of the operation method based on said removed body fluid weight measuring phase and the operation method based on said feed weight measuring phase.

12. The aforementioned blood purifying apparatus operation method, said method comprising alternately repeating the operation method based on the removed body fluid weight measuring phase and the operation method based on the feed weight measuring phase.

Thus, in the blood purifying apparatus and methods of controlling the same in accordance with the invention, the individual reservoir containers (the dialysate reservoir container 9, the replacement fluid reservoir container 10, and the drain reservoir container 8) are weighed by a single weightmeter all at the same time, thereby making it possible to reduce the error in the removal weight of body fluid to the order of 0.2% of the drain fluid weight, as will be described later. This is a significant improvement as compared with the conventional apparatuses of the type whereby each reservoir container is measured individually, where the error can be reduced only to about 2% or so of the drain fluid weight. The error in the feed weight can also be maintained at the same level as that in the conventional apparatuses. Furthermore, since the apparatus of the invention employs only one weightmeter, the overall cost, including that of the control unit, can be significantly reduced.

DESCRIPTION OF THE PREFERRED EMBODIMENTS

A blood purifying apparatus of the invention will be hereafter described with reference made to the accompanying drawings. FIG. 1 schematically shows an embodiment of the blood purifying apparatus of the invention. Apparatus 50 is basically the same as the apparatus shown in FIG. 3. Namely, the apparatus 50 is adapted for the continuous hemodiafiltration (CHDF) method combining continuous hemofiltration (CHF) and continuous hemodialysis (CHD). In FIG. 1, constituent members with the same functions as those of the constituent members shown in FIG. 3 are identified by similar reference characters.

As in the conventional apparatus shown in FIG. 3, the blood purifying apparatus 50 is comprised of a blood drawing line 3 and a blood retransfusing line 4 constituting a blood circulation path; a drain means C for discharging water containing waste products, for example; replacement fluid feed means B connected to the blood retransfusing line 4 for injecting a replacement fluid to the patient; and a dialysate feed means A for feeding a dialysate to the filtrate side within a blood purifying device 2. In the blood drawing line 3, there is provided a blood pump 1, and between the blood drawing line 3 and the blood retransfusing line 4, there is disposed the blood purifying device 2 accommodating a filtration membrane M.

The drain means C is a means for discharging a filtrate and dialysis drain fluid from the blood purifying device 2. The drain means C includes a drain line 23 with one end connected to the blood purifying device 2 and the other end opened; a drain transfer pump 5 disposed in the line; a drain reservoir container 8 connected to a drain branch line 17 branching off from the drain line on the outlet side of the drain transfer pump 5; and a shutoff valve 14 attached to the drain line 23 downstream of the branching portion. The drain reservoir container 8 is equipped with a fluid level sensor 11 for detecting the filled quantity in the drain reservoir container 8. The drain transfer pump 5 discharges a filtrate in the case where the present apparatus is used for CHF, or a dialysate in the case where CHD is employed.

The dialysate feed means A is a means of feeding a dialysate to the filtrate side within the blood purifying device 2. It includes a dialysate transfer line 24 of which one end is connected to the blood purifying device 2 and the other end connected to a dialysate reservoir unit 21; a dialysate transfer pump 6 disposed in the line; a dialysate reservoir container 9 connected to a dialysate branch line 18 branching off on the inlet side of the dialysate transfer pump 6; and a shutoff valve 15 attached to the dialysate transfer line 24 upstream of the branching portion. The dialysate reservoir container 9 is also equipped with a fluid level sensor 12 for detecting the filled quantity in the dialysate reservoir container 9. While the dialysate transfer pump 6 operates to deliver a dialysate to the filtrate side within the blood purifying device 2 when the apparatus is used for CHD, the pump is turned off when the apparatus is used for CHF.

The replacement fluid feed means B is a means of feeding a replacement fluid to the patient, and it includes a replacement fluid line 25 of which one end is connected to the blood retransfusing line 4 and the other end connected to a replacement fluid reservoir unit 22; a replacement fluid transfer pump 7 disposed in the line; a replacement fluid reservoir container 10 connected to a replacement fluid branch line 19 branching off at an inlet side of the replacement fluid transfer pump 7; and a shutoff valve 16 attached to the replacement fluid line 25 upstream of the branching portion. The replacement fluid reservoir container 10 is also equipped with a fluid level sensor 13 for detecting the filled quantity in the replacement fluid reservoir container 10. Although the replacement fluid transfer pump 7 is operated to feed a replacement fluid to the blood supplied from the blood purifying device 2 even when the present apparatus is used for CHF, the pump is turned off when CHD is employed.

As described above, the reservoir containers 8, 9, and 10 of the invention are equipped with the fluid level sensors 11, 12, and 13, respectively. The fluid level sensors 11, 12, and 13, which detect a change in the level of the reservoir containers 8, 9, and 10, respectively, are not particularly limited in terms of their detection principle. Thus, they may be comprised of any of the known components, such as float switches, photoelectric sensors, ultrasound-transmitting bubble detectors, or capacitance-type proximity sensors, for example.

Preferably, the fluid level sensors 11, 12, and 13 detect an upper limit of the level in the reservoir containers 8, 9, and 10, respectively, so as to prevent an overflow, and they are mounted on an upper part of the reservoir containers 8, 9, and 10, respectively. This is because the weighing is carried out by raising or lowering the fluid level in each of the reservoir containers 8, 9, and 10 to a certain level. If the fluid level sensors were to be disposed each at an upper and a lower portion of the reservoir container, and if the fluid level sensors were to be used at the beginning and end of the weighing, the rate of change of the level would vary depending on the flow rate, resulting in a large difference in a single-weighing time between a high flow rate and a low flow rate. As a result, response would be slower in the case of a low flow rate where the weighing time would be longer, and the measurement accuracy would drop in the case of a high flow rate where the weighing time would be shorter. Thus, an upper limit of the level is mechanically detected by the fluid level sensors 11, 12, and 13, and, as regards the lower limit, a reduction amount or a reduction time of the fluid may be set in advance in accordance with the flow rate at the time of use. Alternatively, a reduction rate of the fluid may be set in advance by also taking into consideration the capacity of the reservoir container. In this way, the apparatus can handle any flow rate without moving the position of the fluid level sensor or changing the capacity of the reservoir containers, which is particularly suitable for the continuous and slow treatment method that involves a wide range of flow rates from small to large flow rates. It should be noted, however, that the fluid level sensor attached to the drain reservoir container 8 may preferably be adapted to detect a lower limit of the level, as will be described later.

As in the apparatus shown in FIG. 3, the blood taken out of the patient by the blood pump 1 passes through the blood drawing line 3 and is then introduced into the blood purifying device 2 accommodating the filtration membrane M, where waste products or the like are removed. In the blood purifying device 2, a dialysate is supplied by the dialysate transfer pump 6 and an acid-base equilibrium is achieved by osmosis, for example. The filtrate and dialysis drain fluid are discharged by the drain transfer pump 5. To the blood that has been subjected to filtration and dialysis in the blood purifying device 2, a replacement fluid of substantially the same quantity as that of the aforementioned filtrate is added by the replacement fluid transfer pump 7 as the blood is transported back to the patient via the blood retransfusing line 4, thereby injecting the replacement fluid to the patient.

The blood purifying apparatus 50 of the present embodiment includes a weightmeter 20 that weighs the individual reservoir containers, namely the drain reservoir container 8, the dialysate reservoir container 9, and the replacement fluid reservoir container 10, all at the same time. The weightmeter 20 is produced in accordance with the following design criteria. Namely, any of the values obtained $(W_8-W_9)/W$, $(W_8-W_{10})/W$, and $(W_9-W_{10})/W$ is a small value on the order of $1/1000$, for example, where $W_8(g)$ is the measurement value of the weightmeter 20 when a fluid of $W(g)$ is put in the drain reservoir container 8 while emptying the dialysate reservoir container 9 and the replacement fluid reservoir container 10, $W_9(g)$ is the measurement value of the weightmeter 20 when a fluid of $W(g)$ is put in the dialysate reservoir container 9 while emptying the drain reservoir container 8 and the replacement fluid reservoir container 10, and $W_{10}(g)$ is the measurement value of the weightmeter 20 when a fluid of $W(g)$ is put in the replacement fluid reservoir container 10 while emptying the drain reservoir container 8 and the dialysate reservoir container 9. The error with respect to the actual weight, such as $(W-W_8)/W$, $(W-W_9)/W$, or $(W-W_{10})/W$, may sufficiently be about $5/100$ or smaller. In other words, although the most important thing is not to have variations in the measurement value regardless of in which of the reservoir containers 8, 9, and 10 the fluid is put, the values of $(W_8-W_9)/W$, $(W_8-W_{10})/W$, and $(W_9-W_{10})/W$ can be made about $1/1000$ or smaller because all of the reservoir containers 8, 9, and 10 are measured by the same weightmeter 20.

Hereafter, the operation of the blood purifying apparatus 50 is described. The operation includes a "removed body fluid weight measuring phase" consisting of a first and a second phase, and a "feed weight measuring phase" consisting of a third and a fourth phase, the various phases being appropriately combined when the apparatus 50 is controlled.

In the first phase, the shutoff valves 14, 15, and 16 are opened, and the blood pump 1 and the individual transfer pumps 5, 6, and 7 are operated with a set flow rate. As a result, the filtrate that has remained in the drain reservoir container 8 is discharged via the drain branch line 17 and the line 23 due to the drop. To the dialysate reservoir container 9 and the replacement fluid reservoir container 10, there are poured the dialysate and the replacement fluid from the dialysate reservoir unit 21 and the replacement fluid reservoir unit 22, respectively, due to the drop, via the dialysate branch line 18 and the replacement fluid branch line 19, respectively.

When the fluid level sensor 12 detects that a predetermined amount has been poured into the dialysate reservoir container 9, a detection signal is supplied to a control unit 30. Thereafter, the opening and closing of the shutoff valve 15 is repeated so as to maintain the fluid weight in the dialysate reservoir container 9. Similarly, when the fluid level sensor 13 detects the end of pouring of a predetermined amount in the replacement fluid reservoir container 10, a detection signal is supplied to the control unit 30, and thereafter the opening and closing of the shutoff valve 16 is repeated so as to maintain the fluid weight in the replacement fluid reservoir container 10. After the fluid level sensors 12 and 13 thus detect the completion of the filling of the reservoir containers 9 and 10, the shutoff valve 14 is opened for a certain duration of time, thereby completing the first phase and transitioning to the second phase.

In the second phase, the individual valves 14, 15, and 16 are closed, and then a drain fluid is poured into the drain reservoir container 8 in accordance with the flow rate of the drain transfer pump 5. On the other hand, the fluids in the dialysate reservoir container 9 and the replacement fluid reservoir container 10 are discharged in accordance with the flow rate of the transfer pumps 6 and 7, respectively.

When the completion of pouring of the fluid in the drain reservoir container 8 is detected by the fluid level sensor 11, the second phase is terminated. Alternatively, the second phase may be terminated when: the fluid in the drain reservoir container 8 has reached a predetermined ratio of the weight upon completion of the filling, such as 70% or more, as calculated on the basis of the set flow rate of the transfer pump 5; when the fluid in the dialysate reservoir container 9 has dropped below a predetermined ratio of the weight upon completion of the filling, such as 30% or less, as calculated on the basis of the set flow rate of the transfer pump 6; or when the fluid in the replacement fluid reservoir container 10 has dropped below a predetermined ratio of the weight upon completion of the filling, such as 30% or less, as calculated on the basis of the set flow rate of the transfer pump 7. The former, i.e., the control of the second phase based on level detection, is preferable only when the set range of the flow rate of the transfer pumps is narrow for normal dialysis or filtration, for example. The latter, i.e., the control of the phase based on a set value, is particularly preferable when the set range of the flow rate of the transfer pumps is wide for CHF, CHD, and CHDF treatment, for example, such as when the range is 0.01 L/Hr to 12 L/Hr.

When the measurement time between the start to the end of the second phase is $\Delta T$ (sec), the actual flow rate of the drain transfer pump 5 is $Q_f$ (L/sec), the actual flow rate of the dialysate transfer pump 6 is $Q_d$, and the actual flow rate of the replacement fluid transfer pump 7 is $Q_r$, the weight of drain fluid in the drain fluid reservoir container 8 increases by $\Delta T \times Q_f$ in the measurement time, the weight of dialysate in the dialysate reservoir container 9 decreases by $\Delta T \times Q_d$, and the replacement fluid in the replacement fluid reservoir container 10 decreases by $\Delta T \times Q_r$. Thus, when the amount of change in the total weight of the individual reservoir containers 8, 9, and 10 is $\Delta W$, $\Delta W = \Delta T \times (Q_f - Q_r - Q_d)$, which is the removal weight of body fluid in the second phase. By measuring $\Delta W$ with the weightmeter 20, the removal weight of body fluid can be accurately measured.

By automatically repeating the cycle consisting of the first phase, which is a weighing-preparation step, and the second phase ("removed body fluid weight measuring phase"), in which the removal weight of body fluid is measured, the removal weight of body fluid can be intermittently measured in an accurate manner.

Further, in accordance with the invention, the "feed weight measuring phase" consisting of the third and fourth phases is used in combination with the aforementioned "body fluid removal weight weighing phase." In this way, the feed weight, which is the sum of the weights of the replacement fluid and the dialysate, can be measured, in addition to the measurement of the removal weight of body fluid.

The third phase proceeds in the same way as the first phase, and it ends when the fluid level sensors 12 and 13 detect the end of the filling of the reservoir containers 8 and 9 and the shutoff valve 14 is opened for a certain duration of time.

In the fourth phase, the shutoff valve 14 is opened while the shutoff valves 15 and 16 are closed. When the shutoff valve 14 is open, no fluid enters the drain reservoir container 8. On the other hand, when the shutoff valves 15 and 16 are closed, the fluids in the dialysate reservoir container 9 and the replacement fluid reservoir container 10 are discharged in accordance with the flow rate of the transfer pumps 6 and 7, respectively. The fourth phase is terminated when the fluid in the dialysate reservoir container 9 or the replacement fluid reservoir container 10 dropped below a predetermined ratio of the weight at the end of filling, such as 30% or less, as calculated from the set flow rate of the transfer pumps 6 and 7.

When the measurement time between the start to the end of the fourth phase is $\Delta T$ (sec), the actual flow rate of the dialysate transfer pump 6 is $Q_d$ and the actual flow rate of the replacement fluid transfer pump 7 is $Q_r$, the weight of drain fluid in the drain fluid reservoir container 8 does not change at all in the measurement time, while the weight of dialysate in the dialysate reservoir container 9 decreases by $\Delta T \times Q_d$ and that of the replacement fluid in the replacement fluid reservoir container 10 decreases by $\Delta T \times Q_r$. When the amount of change in the total weight of the individual reservoir containers 8, 9, and 10 is $\Delta W$, $\Delta W = \Delta T \times (0 - Q_r - Q_d)$, or $\Delta T \times (Q_r + Q_d)$, which is $-\Delta W$. Thus, $-\Delta W$ is the "replacement fluid weight+ dialysate weight" in the fourth phase. By measuring $-\Delta W$ with the weightmeter 20, the "replacement fluid weight+ dialysate weight" (the feed weight) can be accurately measured.

Thus, a single cycle consists of the third phase, which is the weighing preparation step, followed by the fourth phase, in which the "replacement fluid weight+dialysate weight" is measured. This cycle is referred to as the "feed weight measuring phase." By automatically repeating the cycle, the feed weight can be intermittently measured in an accurate manner.

During the transition from the first to the second phase (or from the third to the fourth phase), another embodiment may be adopted, as will be described below with reference made to FIG. 2. In this embodiment, although the fluid level sensors 12 and 13 for the dialysate reservoir container 9 and the replacement fluid reservoir container 10 are each attached to an upper portion of the reservoir containers 9 and 10, respectively, the fluid level sensor 11 for the drain reservoir container 8 is attached to the drain branch line 17 so as to detect that the drain reservoir container 8 is completely empty. Alternatively, the fluid level sensor 11 may be attached to a lower portion of the drain reservoir container 8, though not shown, so as to detect a lower limit thereof.

In this embodiment, the apparatus is controlled in the same manner as described with reference to FIG. 1 until the fluid level sensors 12 and 13 for the dialysate reservoir container 9 and the replacement fluid reservoir container 10 detect that the respective containers have been filled to a predetermined amount in the first phase. When the fluid level sensor 11 attached to the drain reservoir container 8 detects a lower limit level, the first phase is presumed to have ended, thereafter moving to the above-described second phase. In the second phase and afterwards, the removal weight of body fluid is weighed in the same manner as in the case of the apparatus shown in FIG. 1. The same procedure may be adopted during the transition from the third phase to the fourth phase. In this way, it can be known whether the fluid collected in the drain reservoir container 8 has been completely discharged, so that the time of the first phase can be advantageously reduced.

In an actual operation of the apparatus of the invention, by combining the "removed body fluid weight measuring phase" and the "feed weight measuring phase," a more accurate delivery management can be performed. The combination of the two phases is not particularly limited, and so they may be combined in any desired manner. Thus, a sequence may be selected from a variety of combinations depending on the objective and the state of operation of the apparatus. For example, the sequence may consist of an alternate repetition of the "removed body fluid weight measuring phase" and the "feed weight measuring phase"; it may consist of one phase continued and then followed by the other phase; or it may be completely randomized. In a specific example, the "removed-water weighing phase" may be repeated in the early stages of operation, and the "feed weight measuring phase" may take part somewhere along the sequence. In another example, the "removed body fluid weight measuring phase" and the "feed weight measuring phase" may comprise the sequence at the ratio of 3 to 1. However, a sequence is preferably such that the "removed body fluid weight measuring phase" and the "feed weight measuring phase" are alternately repeated, as this would enable the removal weight of body fluid and the feed weight to be corrected at the same proportions and because the phases can be easily set.

In accordance with the invention, the manner of controlling the valves or the like is not limited to the above descriptions, and it is only necessary that the amount of change in the total weight of the reservoir containers 8, 9, and 10 can be measured by the weightmeter 20 all at the same time in the second and the fourth phase.

Furthermore, in the blood purifying apparatus of the invention, since the removal weight of body fluid can be accurately weighed, the removal weight of body fluid can be accurately controlled by controlling the rotation speed of at least one transfer pump such that a set removal weight of body fluid is equal to the measured removal weight of body fluid. For example, every time the second phase ends, a set removal weight of body fluid $V_{ref}$ that is converted from the set flow rate and a cumulative weight $V_{mes}$ of the measured removal weight of body fluids are calculated. If $(V_{ref} - V_{mes})$ is positive, the rotation speed of the drain transfer pump 5 is increased, while if $(V_{ref} - V_{mes})$ is negative, the rotation speed of the transfer pump 5 is decreased. In this way, the removal weight of body fluid can be accurately controlled. Alternatively, instead of controlling the rotation speed of the drain transfer pump 5, the flow rate may also be corrected by controlling the rotation speed of the dialysate pump 6 or that of the drain replacement fluid transfer pump 7 to be lower or higher.

Since the "replacement fluid weight+dialysate weight" (feed weight) can be accurately controlled, it is also possible to correct the flow rate of the replacement fluid and the dialysate by decreasing or increasing the rotation speed of the transfer pumps 6 and 7 such that the set flow rate and the measured flow rate coincide. Furthermore, upon correction of the flow rates of the replacement fluid and the dialysate, by making a correction to the drain transfer pump 5 equivalent to the correction made to the transfer pumps 6 and 7, the accuracy of body fluid removal that is accurately controlled at the end of the second phase can be maintained.

The timing of the aforementioned correction is selected such that the removal weight of body fluid is corrected each time the second phase ends while correcting the feed weight each time the fourth phase ends, for example. This method is preferable in systems in which the "removed body fluid weight measuring phase" is repeated at the initial stages of operation and thereafter the "feed weight measuring phase" is initiated somewhere along the sequence. Alternatively, the correction may be made after repeating a series of phases for several times. This method is preferable when the flow rate is desired to be slowly followed, for example. Further alternatively, a method may be employed whereby the transfer pumps 5, 6, and 7 are corrected all at the same time such that the feed weight and the removal weight of body fluid coincide, after the end of the entire series of phases. This method is preferable in systems where the "removed-water weighing phase" and the "feed weight measuring phase" are alternately repeated. In any of these methods, the timing of correction is not particularly limited and it is only necessary that it is performed outside the second and the fourth phases, in which weighing is carried out.

Thus, there is only one weightmeter employed, and by simply controlling the rotation of the pumps using the control unit, the removal weight of body fluid or the feed weight can be accurately controlled. Thus, in addition to the accuracy of control, the structure of the apparatus can be advantageously simplified.

Although the above-described examples involved CHDF, it should be obvious to those skilled in the art that the invention is not limited to CHDF in view of the fact that the apparatus performs CHF when the flow rate of the dialysate transfer pump is set to zero, while it performs CHD when the flow rate of the replacement fluid transfer pump is set to zero. It goes without saying that the blood purifying apparatus of the invention can also be used for conventional hemodialysis, hemofiltration, and hemodiafiltration, in addition to the above-described CHDF, CHF, and CHD.

INDUSTRIAL APPLICABILITY

As described above, the invention enables the feed weight to be controlled with higher accuracy than is possible with conventional technique, not to mention the removal weight of body fluid, which is the most important parameter in patient management. Further, the structure of the apparatus can be simplified. The apparatus of the invention does not require frequent weighing and adjustment operations by staff as in the conventional apparatuses, so that the treatment of the patient can be continued safely while controlling the body fluid weight of the patient properly. Another advantage is that the dialysate reservoir unit or the replacement fluid reservoir unit can be exchanged as needed, or, in cases where the filtrate and the dialysis drain fluid are stored in tanks, for example, the tanks can be exchanged as needed, without directly affecting the measurement of the removal weight of body fluid or the feed weight, and without terminating the treatment.

The invention claimed is:

1. A blood purifying apparatus comprising a dialysate feed means, a replacement fluid feed means, a drain means, a blood purifying device, and a blood circulation path consisting of a blood drawing line and a blood retransfusing line, wherein:

said dialysate feed means comprises: a dialysate transfer line of which one end is connected to said blood purifying device and the other end connected to a dialysate reservoir unit; a dialysate transfer pump disposed in said dialysate transfer line; a dialysate reservoir container connected to a dialysate branch line branching off on an inlet side of said dialysate transfer pump; and a first shutoff valve attached to said dialysate transfer line upstream of a branch portion;

said replacement fluid feed means comprises: a replacement fluid feeding line of which one end is connected to said blood retransfusing line and the other end connected to a replacement fluid reservoir unit; a replacement fluid transfer pump disposed in said replacement fluid feeding line; a replacement fluid reservoir container connected to a replacement fluid branch line branching off on an inlet side of said replacement fluid transfer pump; and a second shutoff valve attached to said replacement fluid transfer line upstream of a branch portion;

said drain means comprises: a drain line of which one end is connected to said blood purifying device and the other end opened; a drain transfer pump disposed in said drain line; a drain reservoir container connected to a drain branch line branching off on an outlet side of said drain transfer pump; and a third shutoff valve attached to said drain line downstream of a branch portion, wherein the dialysate reservoir container, the replacement fluid reservoir container and the drain reservoir container are each equipped with a fluid level sensor, said apparatus further comprising a weightmeter for weighing the dialysate reservoir container, the replacement fluid reservoir container and the drain reservoir container at once, and a control unit for controlling the opening and closing of said first, second and third shutoff valves and the pump flow rate of each of said dialysate transfer pump, said replacement fluid transfer pump and said drain transfer pump, wherein said control unit performs a removed body fluid weight measuring phase consisting of:

a first phase in which the first, second and third shutoff valves are opened, whereby said dialysate reservoir container and said replacement fluid reservoir container are each filled with a fluid while at the same time a fluid is discharged from said drain reservoir container; and a second phase in which said apparatus is controlled with each of said first, second and third shutoff valves closed, and a change in the total fluid weight in said dialysate reservoir container, said replacement fluid reservoir container, and said drain reservoir container during the operation of said apparatus is acquired from information provided by said weightmeter in order to weigh the removal weight of body fluid, wherein said control unit controls the flow rate of at least one of said dialysate transfer pump, said replacement fluid transfer pump and said drain transfer pump such that a desired water-removed weight can be obtained in said second phase.

2. The blood purifying apparatus according to claim 1, wherein said control unit performs a feed weight measuring phase consisting of:

a third phase in which each of said first, second and third shutoff valves is opened, whereby said dialysate reservoir container and said replacement fluid reservoir container are filled with individual fluids while at the same time a fluid is discharged from said drain reservoir container; and a fourth phase in which said apparatus is controlled with only the first shutoff valve and the second shutoff valve closed, and in which a change in the total fluid weight in said dialysate reservoir container, said replacement fluid reservoir container, and said drain reservoir container is acquired from information provided by said weightmeter so as to calculate a feed weight which is the sum of the weight of replacement fluid and the weight of the dialysate, wherein said control unit controls the flow rate of the dialysate transfer pump and the replacement fluid transfer pump such that a desired feed weight can be obtained during the fourth phase.

3. The blood purifying apparatus according to claim 2, wherein said control unit controls the flow rate of at least one of the dialysate transfer pump, the replacement fluid transfer pump and the drain transfer pump based on an arbitrary combination of said removed body fluid weight measuring phase and said feed weight measuring phase.

4. The blood purifying apparatus according to claim 2, wherein said control unit controls the flow rate of at least one of the dialysate transfer pump, the replacement fluid transfer pump and the drain transfer pump by alternately repeating said removed body fluid weight measuring phase and said feed weight measuring phase.

5. A method of controlling a blood purifying apparatus, said apparatus comprising a dialysate feed means, a replacement fluid feed means, a drain means, a blood purifying device, and a blood circulation path consisting of a blood drawing line and a blood retransfusing line, wherein:

said dialysate feed means comprises: a dialysate transfer line of which one end is connected to said blood purifying device and the other end connected to a dialysate reservoir unit; a dialysate transfer pump disposed in said dialysate transfer line; a dialysate reservoir container connected to a dialysate branch line branching off on an inlet side of said dialysate transfer pump; and a first shutoff valve attached to said dialysate transfer line upstream of a branch portion;

said replacement fluid feed means comprises: a replacement fluid feeding line of which one end is connected to said blood retransfusing line and the other end connected to a replacement fluid reservoir unit; a replacement fluid transfer pump disposed in said replacement fluid feed line; a replacement fluid reservoir container connected to a replacement fluid branch line branching off on an inlet side of said replacement fluid transfer pump; and a second shutoff valve attached to said replacement fluid transfer line upstream of a branch portion;

said drain means comprises: a drain line of which one end is connected to said blood purifying device and the other end opened; a drain transfer pump disposed in said drain line; a drain reservoir container connected to a drain branch line branching off on an outlet side of said drain transfer pump; and a third shutoff valve attached to said drain line downstream of a branch portion, wherein the dialysate reservoir container, the replacement fluid reservoir container and the drain reservoir container are each equipped with a fluid level sensor, said apparatus further comprising a weightmeter for weighing the dialysate reservoir container, the replacement fluid reservoir container and the drain reservoir container at once, and a control unit for controlling the opening and closing of said first, second and third shutoff valves and the pump flow rate of each of said dialysate transfer pump, said replacement fluid transfer pump and said drain transfer pump, said method comprising performing a removed body fluid weight measuring phase consisting of:

a first phase of opening the first, second and third shutoff valves, whereby said dialysate reservoir container and said replacement fluid reservoir container are each filled with a fluid while at the same time a fluid is discharged from said drain reservoir container; and a second phase of closing each of said first, second and third shutoff valves, and acquiring a change in the total fluid weight in said dialysate reservoir container, said replacement fluid reservoir container, and said drain reservoir container during the operation of said apparatus from information provided by said weightmeter in order to weigh the removal weight of body fluid, wherein said control unit controls the flow rate of at least one of said dialysate transfer pump, said replacement fluid transfer pump and said drain transfer pump such that a desired removal weight of body fluid can be obtained in said second phase.

6. A method of controlling a blood purifying apparatus, said apparatus comprising a dialysate feed means, a replacement fluid feed means, a drain means, a blood purifying device, and a blood circulation path consisting of a blood drawing line and a blood retransfusing line, wherein:

said dialysate feed means comprises: a dialysate transfer line of which one end is connected to said blood purifying device and the other end connected to a dialysate reservoir unit; a dialysate transfer pump disposed in said dialysate transfer line; a dialysate reservoir container connected to a dialysate branch line branching off on an inlet side of said dialysate transfer pump; and a first shutoff valve attached to said dialysate transfer line upstream of a branch portion;

said replacement fluid feed means comprises: a replacement fluid feeding line of which one end is connected to said blood retransfusing line and the other end connected to a replacement fluid reservoir unit; a replacement fluid transfer pump disposed in said replacement fluid feeding line; a replacement fluid reservoir container connected to a replacement fluid branch line branching off on an inlet side of said replacement fluid transfer pump; and a second shutoff valve attached to said replacement fluid transfer line upstream of a branch portion;

said drain means comprises: a drain line of which one end is connected to said blood purifying device and the other end opened; a drain transfer pump disposed in said drain line; a drain reservoir container connected to a drain branch line branching off on an outlet side of said drain transfer pump; and a third shutoff valve attached to said drain line downstream of a branch portion, wherein the dialysate reservoir container, the replacement reservoir container and the drain reservoir container are each equipped with a fluid level sensor, said apparatus further comprising a weightmeter for weighing the dialysate reservoir container, the replacement fluid reservoir container and the drain reservoir container at once, and a control unit for controlling the opening and closing of said first, second and third shutoff valves and the pump flow rate of each of said dialysate transfer pump, said replacement fluid transfer pump and said drain transfer pump, said method comprising performing a feed weight measuring phase consisting of:

a first phase of opening each of said first, second and third shutoff valves whereby said dialysate reservoir container and said replacement fluid reservoir container are filled with individual fluids while at the same time discharging a fluid from said drain reservoir container; and a second phase of controlling said apparatus by closing only the first shutoff valve and the second shutoff valve, and acquiring a change in the total fluid weight in said dialysate reservoir container, said replacement fluid reservoir container, and said drain reservoir container from information provided by said weightmeter so as to calculate a feed weight which is the sum of the weight of replacement fluid and the weight of the dialysate, wherein said control unit controls the flow rate of at least one of said dialysate transfer pump, said replacement fluid transfer pump and said drain transfer pump such that a desired feed weight can be obtained during the second phase.

7. The method of controlling the blood purifying apparatus according to claim 5, said control method further comprising:

arbitrarily combining the control method based on performing the removed body fluid weight measuring phase and based on performing a feed weight measuring phase, said feed weight measuring phase consisting of:

a third phase of opening each of said first, second and third shutoff valves whereby said dialysate reservoir container and said replacement fluid reservoir container are filled with individual fluids while at the same time discharging a fluid from said drain reservoir container; and a fourth phase of controlling said apparatus by closing only the first shutoff valve and the second shutoff valve, and acquiring a change in total fluid weight in said dialysate reservoir container, said replacement fluid reservoir container, and said drain reservoir container from information provided by said weightmeter so as to calculate a feed weight which is the sum of the weight of replacement fluid and the weight of the dialysate, wherein said control unit controls the flow rate of at least one of said dialysate transfer pump, said replacement fluid transfer pump and said drain transfer pump such that a desired feed weight can be obtained during the fourth phase.

8. The method of controlling the blood purifying apparatus according to claim 5, said control method further comprising:

alternately repeating the control method based on performing the removed body fluid weight measuring phase and based on performing a feed weight measuring phase, said feed weight measuring phase consisting of:

a third phase of opening each of said first, second and third shutoff valves whereby said dialysate reservoir container and said replacement fluid reservoir container are filled with individual fluids while at the same time discharging a fluid from said drain reservoir container; and a fourth phase of controlling said apparatus by closing only the first shutoff valve and the second shutoff valve, and acquiring a change in total fluid weight in said dialysate reservoir container, said replacement fluid reservoir container, and said drain reservoir container from information provided by said weightmeter so as to calculate a feed weight which is the sum of the weight of replacement fluid and the weight of the dialysate, wherein said control unit controls the flow rate of at least one of said dialysate transfer pump, said replacement fluid transfer pump and said drain transfer pump such that a desired feed weight can be obtained during the fourth phase.

9. A blood purifying apparatus comprising a dialysate feed means, a replacement fluid feed means, a drain means, a blood purifying device, and a blood circulation path consisting of a blood drawing line and a blood retransfusing line, wherein:

said dialysate feed means comprises: a dialysate transfer line of which one end is connected to said blood purifying device and the other end connected to a dialysate reservoir unit; a dialysate transfer pump disposed in said line; a dialysate reservoir container connected to a dialysate branch line branching off on an inlet side of said dialysate transfer pump; and a first shutoff valve attached to said dialysate transfer line upstream of a branch portion;

said replacement fluid feed means comprises: a replacement fluid feeding line of which one end is connected to said blood retransfusing line and the other end connected to a replacement fluid reservoir unit; a replacement fluid transfer pump disposed in said line; a replacement fluid reservoir container connected to a replacement fluid branch line branching off on an inlet side of said replacement fluid transfer pump; and a second shutoff valve attached to said replacement fluid transfer line upstream of a branch portion;

said drain means comprises: a drain line of which one end is connected to said blood purifying device and the other end opened; a drain transfer pump disposed in said line; a drain reservoir container connected to a drain branch line branching off on an outlet side of said drain transfer pump; and a third shutoff valve attached to said drain transfer line downstream of a branch portion, wherein the dialysate reservoir container, the replacement fluid reservoir container and the drain reservoir container are each equipped with a fluid level sensor, said apparatus further comprising a weightmeter for weighing the dialysate reservoir container, the replacement fluid reservoir container and the drain reservoir container at once, and a control unit for controlling the opening and closing of said first, second and third shutoff valves and the pump flow rate of each of said dialysate transfer pump, said replacement fluid transfer pump and said drain transfer pump, wherein said control unit performs a feed weight measuring phase consisting of:

a first phase in which each of said first, second and third shutoff valves is opened, whereby said dialysate reservoir container and said replacement fluid reservoir container are filled with individual fluids while at the same time a fluid is discharged from said drain reservoir container; and a second phase in which said apparatus is controlled with only the first shutoff valve and the second shutoff valve closed, and in which a change in the total fluid weight in said dialysate reservoir container, said replacement fluid reservoir container, and said drain reservoir container is acquired from information provided by said weightmeter so as to calculate a feed weight which is the sum of the weight of replacement fluid and the weight of the dialysate, wherein said control unit controls the flow rate of the dialysate transfer pump and the replacement fluid transfer pump such that a desired feed weight can be obtained during the second phase.

* * * * *

UNITED STATES PATENT AND TRADEMARK OFFICE
CERTIFICATE OF CORRECTION

| | |
|---|---|
| PATENT NO. | : 7,618,542 B2 |
| APPLICATION NO. | : 10/523968 |
| DATED | : November 17, 2009 |
| INVENTOR(S) | : Soichirou Okazaki |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 971 days.

Signed and Sealed this

Fourteenth Day of December, 2010

David J. Kappos
*Director of the United States Patent and Trademark Office*